United States Patent
Adjei et al.

(10) Patent No.: US 6,461,639 B2
(45) Date of Patent: *Oct. 8, 2002

(54) CORE FORMULATION

(75) Inventors: Akwete L. Adjei, Bridgewater, NJ (US); Yaping Zhu, Highland Park, NJ (US); Anthony J. Cutie, Bridgewater, NJ (US)

(73) Assignee: Aeropharm Technology, Inc., Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,810

(22) Filed: Feb. 15, 2001

(65) Prior Publication Data

US 2001/0036478 A1 Nov. 1, 2001

Related U.S. Application Data

(60) Provisional application No. 60/201,233, filed on May 1, 2000.

(51) Int. Cl.$^7$ ............................. A61K 9/24; A61K 9/28; A61K 9/14

(52) U.S. Cl. ..................... 424/472; 424/474; 424/475; 424/468; 424/489; 424/490; 424/471

(58) Field of Search ................................ 424/489, 472, 424/474, 468, 471, 475, 490; 514/866

(56) References Cited

U.S. PATENT DOCUMENTS

| | | | | |
|---|---|---|---|---|
| 4,389,330 A | * | 6/1983 | Tice et al. | 427/213.36 |
| 6,030,641 A | * | 2/2000 | Yamashita et al. | 424/451 |
| 6,166,042 A | | 12/2000 | Ikeda et al. | 514/342 |
| 6,296,874 B1 | * | 10/2001 | Cutie et al. | 424/474 |

* cited by examiner

*Primary Examiner*—Thurman K. Page
*Assistant Examiner*—Robert M. Joynes
(74) *Attorney, Agent, or Firm*—Frommer Lawrence & Haug LLP

(57) ABSTRACT

This invention relates to a controlled-release combination drug product comprising troglitazone, e.g. its hydrochloride, and a biguamide, e.g. metformin. In particular, the product comprises a core of metformin, at least a portion thereof has a layer or coat thereon of troglitazone.

18 Claims, No Drawings

CORE FORMULATION

This application claims priority from U.S. provisional application Ser. No. 60/201,233, filed May 1, 2000, which is incorporated herein by reference.

BACKGROUND OF THE INVENTION

1. Field of the Invention

This invention relates to a core formulation, and, more particularly, to a core formulation comprising a first layer comprising troglitazone, which covers at least a portion of a core comprising a biguanide, such as for example metformin (i.e., glucophage), with a modulating release polymer comprising of a polysacchaside, e.g. an alginate.

2. Description of the Related Art

Metformin and troglitazone, and their salts such as the hydrochlorides, maleates, tartrates, etc., are two active ingredients of anti-diabetic drugs that are used to treat diabetic patients, e.g. human beings. These two active agents are administered orally to patients in need thereof in protocols calling for the single administration of either ingredient. Heretofore, there has not been revealed or hinted at combining both ingredients and certainly not a physically combined core formulation comprising both ingredients. The advantage of such a core formulation is advantageous to patients and prescribers because both medicaments are synergistic to each other in the body when used in the management of blood glucose control, i.e., diabetes. Furthermore, the use of a modulating agent, like an alginate, in the preparation, controls the rate of drug release over a clinically meaningful period to enable better control of the effect of the medicinal agents in such preparation.

SUMMARY OF THE INVENTION

This invention relates to a core formulation, and, more particularly, to a core formulation comprising a first layer comprising troglitazone or a derivative thereof, e.g. troglitazone hydrochloride, which covers at least a portion of a core comprising a biguanide, one of both of which are intimately dispersed in a polysacchaside modulating release agent, e.g. an alginate.

DETAILED DESCRIPTION OF THE INVENTION

A typical biguanide is metformin. It typically is used clinically as a pharmaceutically acceptable salt, preferably the hydrochloride salt. A commercial form of metformin hydrochloride is available as glucophage. Its chemical name is N,N-dimethylimidodicarbonimidic diamide hydrochloride. Metformin hydrochloride is a hydrochloride salt of metformin base, and as used herein, "metformin" means the base compound as well as its pharmaceutically acceptable salts. Metformin is used clinically to manage non-insulin dependent diabetes mellitus ("NIDDM"), particularly in patients who are not effectively treated with a sulfonylurea. While it is not chemically related to the sulfonylureas, it is routinely utilized in combination with a sulfonylurea, and has been shown to be synergistic in some cases. Other biguanides such as phenformin, buformin etc. can also be used. Additionally, in the treatment of a diabetic patient the metformin and the troglitazone, e.g. its hydrochloride, are present in effective amounts to provide such treatment.

Metformin is an active ingredient for a commercially available drug employed to treat diabetes mellitus in a host or mammal, e.g. a human being, another animal. The typical daily effective dose for the oral treatment of a mammal, i.e., a human, ranges from about 500 mg to about 2550 mg. Typically, the dose is a single dose of about 500 mg to about 850 mg.

Alginates are pharmaceutical excipients generally regarded as safe and used therefore to prepare a variety of pharmaceutical systems well documented in the patent literature [S. Bloor, U.S. Pat. No. 6,166,084, Compositions for the treatment of chronic wounds; Ikeda, et al., U.S. Pat. No. 6,166,043, Pharmaceutical composition; Ikeda, et al., U.S. Pat. No. 6,166,042, Pharmaceutical composition, Fassler, et al., U.S. Pat. No. 6,166,004, Combinations of HIV protease inhibitors with reverse transcriptase inhibitors; Itakura, et al., U.S. Pat. No. 6,165,615, Gradual-releasing capsule and method for manufacturing the same].

A typical alginate modulating releasing agent is ammonium calcium alginate. It is typically used in injectable implants and microsphere preparations for controlled release. A commercial form of ammonium calcium alginate is Keltose, manufactured and distributed by ISP (International Specialty Products, 1361 Alps Road, Wayne, N.J. 07470). As used herein, "alginate" means alginic acid, or any of its salts.

Troglitazone hydrochloride, (Rezulin®), is an active ingredient for a commercially available drug employed to treat diabetes mellitus in a host, e.g. a human being. The typical daily effective dose for the oral administration to a mammal, e.g. a human being, ranges from about 200 mg to about 400 mg, given as a single dose.

Heretofore, the alginate modulating agents with the hypoglycemic drugs metformin and troglitazone hydrochloride have, not been administered together to try to improve the control and effectiveness of either drug, although co-administration of the two has been proposed [Whitcomb; et al., U.S. Pat. No. 6,011,049]. However, a combined form of the drugs, i.e. a single integral unit thereof has not heretofore been reported. The present invention provides such a single integral unit in the form of a core formulation.

As indicated above, the relative concentrations of each drug is such that a first layer comprising troglitazone hydrochloride is prepared. The first layer covers at least a portion of a core comprising metformin with a portion or all of the amount of the alginate. Depending upon the rate of administration of the core preparation, the metabolism of the patient destined to be treated and the desired concentrations of each ingredient for each drug, the first layer may cover only a portion of the core or encompass the entire core. For example, one quarter of the core to about three fourths of the tablet core. The first layer should comprise troglitazone hydrochloride with or without any alginate, because its dose requirement is lower compared to metformin. Additionally, troglitazone hydrochloride is slightly non-polar, its solubility rate is slower, and its absorption rate thus is dependent on its dissolution rate in the contents of the gastrointestinal tract compared with metformin.

It is to be understood, depending upon the desired rate of administration to the patient, either the first layer or the core may additionally contain a mixture of the two active ingredients or both the first layer and the core may contain the two active ingredients with different and varying concentrations of one or both active ingredients.

The first layer of the core comprises troglitazone, e.g. its hydrochloride, in an amount of about 0.01% to about 20% of the total weight of the core formulation, whereas, the metformin in the core is present in an amount of about 10% to about 97.5% of the total weight of the core formulation.

Where combinations of the two active ingredients are present in the first layer and/or the core, the amounts of troglitazone, e.g. its hydrochloride, ranges from about 1 mg to about 45 mg whereas the metformin ranges from about 100 mg to about 2550 mg.

Finally, it is to be understood that a third pharmacologically active material, e.g. a drug, such as for example a sulfonylurea, an α-glucosidase inhibitor, a meglitinide, and an ACE inhibitor can admixed with the active ingredients in the first layer and/or the core.

The alpha.-glucosidase inhibitors [Jean-Bernard Ducep et al., U.S. Pat. No. 5,504,078], bisglucosylmoranoline derivatives [UK Patent No. GB 2 088 365 A], and glucosylmoranoline derivatives [European Patent No. 87112480.6] include the following medicaments: 1.5-Dideoxy-4-O(.alpha.,D-glucopyranosyl)-1,5-[6,7-dideoxy-7-D-glucoheptopyranosyl)imino]-D-glucitol; 1.5-Dideoxy-4-O(.alpha.,D-glucopyranosyl)-1,5-[(1-deoxy-D-fructofuranosyl)imino]-D-glucitol; 1.5-Dideoxy-4-O(.alpha.,D-glucopyranosyl)-1,5[(4-deoxy-4-D-glucopyranosyl)imino]-D-glucitol; 1.5-Dideoxy-4-O(.alpha.,D-glucopyranosyl)-N-[6-deoxy-1-(6-O-D-glucopyranosyl)-.alpha.-D-glucopyranosyl]-1.5-imino-D-glucitol; 1,5-Dideoxy-4-O(.alpha.,D-glucopyranosyl)-N-[6,7-dideoxy-1-(6-O-D-glucopyranosyl)-7-.alpha.-D-glucoheptopyranosyl]-1,5-imino-D-glucitol; 1.5-Dideoxy-4-O(.alpha.,D-glucopyranosyl)-1,5[(4-deoxy-4-D-glucopyranosyl)methylimino]-D-glucitol; 1.5-Dideoxy-4-O(.alpha.,D-glucopyranosyl)-N-[4-deoxy-1-(4-O-D-glucopyranosyl)-.alpha.-D-glucopyranosyl]-1,5-imino-D-glucitol; 1.5-Dideoxy-4-O(.alpha.,D-glucopyranosyl)-1,5-{[2(1-D-arabinofuranose)ethyl]imino}-D-glucitol; 1.5-Dideoxy-4-O(.alpha.,D-glucopyranosyl)-N-[4-deoxy-1-(6-O-D-glucopyranosyl)-.alpha.-D-glucopyranosyl]-1,5-imino-D-glucitol; 1.5-Dideoxy-4-O(.alpha.,D-glucopyranosyl)-N-{[4-deoxy-1-(4-O-D-glucopyranosyl)-4-.alpha.-D-glucopyranosyl]methyl}-1,5-imino-D-glucitol; 1.5-Dideoxy-4-O(.alpha.,D-glucopyranosyl)-N-{[4-deoxy-1-(6-O-D-glucopyranosyl)-4-.alpha.-D-glucopyranosyl]methyl}-1,5-imino-D-glucitol; 1.5-Dideoxy-4-O(.alpha.,D-glucopyranosyl)-1,5-[(6-deoxy-1-O-methyl-6-β-D-glucopyranosyl)-imino]-D-glucitol; 1.5-Dideoxy-4-O(.alpha.,D-glucopyranosyl)-1,5-[( 6,7-dideoxy-1-O-methyl-7-β-D-glucoheptopyranosyl)imino]-D-glucitol; 1.5-Dideoxy-4-O(.alpha.,D-glucopyranosyl)-1,5-[(1-deoxy-2-O-methyl-β-D-fructofuranosyl)imino]-D-glucitol, 1.5-Dideoxy-4-O(.alpha.,D-glucopyranosyl)-1,5-[(4-deoxy-1-O-methyl-4-β-D-glucopyranosyl)imino]-D-glucitol; 1.5-Dideoxy-4-O(.alpha.,D-glucopyranosyl)-N-[6-deoxy-1(1-O-methyl-6-O-β-D-glucopyranosyl)-.alpha.-D-glucopyranosyl]-1,5-imino-D-glucitol; 1.5-Dideoxy-4-O(.alpha.,D-glucopyranosyl)-N-[6,7-dideoxy-1(1-O-methyl-6-O-β-D-glucopyranosyl)-7-.alpha.-D-glucoheptopyranosyl]-1,5-imino-D-glucitol; 1.5-Dideoxy-4-O(.alpha.,D-glucopyranosyl)-1,5-[(4-deoxy-1-O-methyl-4-β-D-glucopyranosyl)methylimino]-D-glucitol; 1.5-Dideoxy-4-O(.alpha.,D-glucopyranosyl)-N-[4-deoxy-1-(1-O-methyl-4-O-8-D-glucopyranosyl)-.alpha.-D-glucopyranosyl]-1,5-imino-D-glucitol; 1,5-Dideoxy-4-O(.alpha.,D-glucopyranosyl)-1,5-{[2-(1-O-methyl-1-β-D-arabinofuranosyl)ethyl]imino}-D-glucitol; 1,5-Dideoxy-4-O(.alpha.,D-glucopyranosyl)-N-[4-deoxy-1-(1-O-methyl-6-O-β-D-glucopyranosyl)-.alpha.-D-glucopyranosyl]-1,5-imino-D-glucitol; 1,5-Dideoxy-4-O(.alpha.,D-glucopyranosyl)-N-{[4-deoxy-1-(1-O-methyl-4-O-β-D-glucopyranosyl)-4-.alpha.-D-glucopyranosyl]methyl}-1,5-imino-D-glucitol; 1,5-Dideoxy-4-O(.alpha.,D-glucopyranosyl)-N-{[4-deoxy-1-(1-O-methyl-6-O-β-D-glucopyranosyl)-4-.alpha.-D-glucopyranosyl]methyl}-1, 5imino-D-glucitol; 1,5-Dideoxy-6-O(.alpha.,D-glucopyranosyl)-1,5-[6,7-dideoxy-7-D-glucoheptopyranosyl)imino]-D-glucitol; 1,5-Dideoxy-6-O(.alpha.,D-glucopyranosyl)-1,5-[(1-deoxy-D-fructofuranosyl)imino]-D-glucitol; 1,5-Dideoxy-6-O(.alpha.,D-glucopyranosyl)-1,5-[(4-deoxy-4-D-glucopyranosyl)imino]-D-glucitol; 1,5-Dideoxy-6-O(.alpha.,D-glucopyranosyl)-N-[6-deoxy-1-(6-O-D-glucopyranosyl)-.alpha.-D-glucopyranosyl]-1,5-imino-D-glucitol; 1.5-Dideoxy-6-O(.alpha.,D-glucopyranosyl)-N-[6,7-dideoxy-1-(6-O-D-glucopyranosyl)-7-.alpha.-D-glucoheptopyranosyl]-1,5-imino-D-glucitol; 1.5-Dideoxy-6-O(.alpha.,D-glucopyranosyl)-1,5-[(4-deoxy- 4-D-glucopyranosyl)methylimino]-D-glucitol; 1.5-Dideoxy-6-O(.alpha.,D-glucopyranosyl)-N-[4-deoxy-1-(4-O-D-glucopyranosyl)-.alpha.-D-glucopyranosyl]-1,5-imino-D-glucitol; 1,5-Dideoxy-6-O(.alpha.,D-glucopyranosyl)-1,5-{[2(1-D-arabinofuranose)ethyl]imino}-D-glucitol; 1,5-Dideoxy-6-O(.alpha.,D-glucopyranosyl)-N-[4-deoxy-1-(6-O-D-glucopyranosyl)-.alpha.-D-glucopyranosyl]-1,5-imino-D-glucitol; 1,5-Dideoxy-6-O(.alpha.,D-glucopyranosyl)-N-{[4-deoxy-1-(4-O-D-glucopyranosyl)-4-.alpha.-D-glucopyranosyl]methyl}-1,5-imino-D-glucitol; 1,5-Dideoxy-6-O(.alpha.,D-glucopyranosyl)-N-{[4-deoxy-1-(6-O-D-glucopyranosyl)-4-.alpha.,D-glucopyranosyl]methyl}-1,5-imino-D-glucitol; 1.5-Dideoxy-6-O(.alpha.,D-glucopyranosyl)-1,5-[(6-deoxy-1-O-methyl-6-β-D-glucopyranosyl)-imino]-D-glucitol; 1,5-Dideoxy-6-O(.alpha.,D-glucopyranosyl)-1,5-[(6,7-dideoxy-1-O-methyl-7-β-D-glucoheptopyranosyl)imino]-D-glucitol; 1,5-Dideoxy-6-O(.alpha.,D-glucopyranosyl)-1,5-[(1-deoxy-2-O-methyl-β-D-fructofuranosyl)imino]-D-glucitol; 1.5-Dideoxy-6-O(.alpha.,D-glucopyranosyl)-1,5-[(4-deoxy-1-O-methyl-4-β-D-glucopyranosyl)imino]-D-glucitol; 1,5-Dideoxy-6-O(.alpha.,D-glucopyranosyl)-N-[6-deoxy-1-(1-O-methyl-6-O-β-D-glucopyranosyl)-.alpha.-D-glucopyranosyl]-1,5-imino-D-glucitol; 1,5-Dideoxy-6-O(.alpha.,D-glucopyranosyl)-N-[6,7-dideoxy-1-(1-O-methyl-6-O-β-D-glucopyranosyl)-7-.alpha.-D-glucoheptopyranosyl]-1,5-imino-D-glucitol; 1,5-Dideoxy-6-O(.alpha.,D-glucopyranosyl)-1,5-[(4-deoxy-1-O-methyl-4-β-D-glucopyranosyl)methylimino]-D-glucitol; 1,5-Dideoxy-6-O(.alpha.,D-glucopyranosyl)-N-[4-deoxy-1-(1-O-methyl-4-O-β-D-glucopyranosyl)-.alpha.-D-glucopyranosyl]-1,5-imino-D-glucitol; 1,5-Dideoxy-6-O(.alpha.,D-glucopyranosyl)-1,5-{[2-(1-O-methyl-1-B-D-arabinofuranosyl)ethyl]imino}-D-glucitol; 1,5-Dideoxy-6-O(.alpha.,D-glucopyranosyl)-N-[4-deoxy-1-(1-O-methyl-6-O-β-D-glucopyranosyl)-.alpha.-D-glucopyranosyl]-1,5-imino-D-glucitol; 1,5-Dideoxy-6-O(.alpha.,D-glucopyranosyl)-N-([4-deoxy-1-(1-O-methyl- 4-O-β-D-glucopyranosyl)-4-.alpha.-D-glucopyranosyl]methyl}-1,5-imino-D-glucitol; 1,5-Dideoxy-6-O(.alpha.,D-glucopyranosyl)-N-([4-deoxy-1-(1-O-methyl-6-O-β-D-glucopyranosyl)-4-.alpha.-D-glucopyranosyl]methyl}-1,5-imino-D-glucitol.

The list of medicaments includes acid addition salt forms with such inorganic acids, such as, for example, hydrochloric, hydrobromic, sulfuric, phosphoric and like acids; with organic carboxylic acids such as, for example, acetic, propionic, glycolic, lactic, pyruvic, malonic, succinic, fumaric, maleic, tartaric, citric, ascorbic, maleic, hydroxymaleic, dihydroxymaleic, benzoic, 2-acetoxybenzoic, mandelic and like acids; and with organic sulfonic acids such as methanesulfonic acid and p-toluenesulfonic acid.

The sulfonylureas are a class of compounds that have been widely employed to treat diabetes. Such compounds are well known, for example, as described in U.S. Pat. Nos. 3,454,635; 3,669,966; 2,968,158; 3,501,495; 3,708,486; 3,668,215; 3,654,357; and 3,097,242. Especially preferred sulfonylureas to be employed in the combinations or core formulations of this invention are glyburide, gliquidone, glipizide, tolbutamide, tolazamide, glisoxepid, chlorpropamide, glibornuride, gliclazide, glimepiride, phenbutamide, and tolcyclamide. Other medicaments, such as, for example, an antibiotic, a vitamin, a drug that works on the heart or in the liver, may be admixed with the active ingredients in the first layer and/or the core.

As indicated above, the modulating polymer, e.g., a polysaccharide, such as alginate salt, such as ammonium calcium alginate, may be associated with the first layer alone or with both the metformin and troglitazone hydrochloride. The type of association as well as the concentration of the modulating agent is dependent upon the concentrations of the core active ingredient and the layer active ingredient, the degree of concentration of the core by the first layer and the desired rate of administration of each active ingredient. Typically, the modulated release agent, e.g. the alginate, is present in an amount ranging from about 10 ppm to about 100,000 ppm.

The resultant core having the first layer thereon is prepared by any conventional means known in the pharmaceutical art, e.g. compression, tabletting technology, spraying technology, or encapsulation in a pharmaceutically acceptable presentation, such as a gelatin capsule. In particular, typically the core formulation of the present invention is preferably fabricated by compression into a tablet.

The resultant core formulation of the present invention is useful to treat diabetes mellitus. Surprisingly the resultant core formulation of the invention is as user friendly and clinically effective as compared to the administration of metformin alone or troglitazone hydrochloride alone as demonstrated by co-administration of the two agents [Whitcomb; et al., U.S. Pat. No. 6,011,049], where in general, the incidence of adverse events was not influenced by age or menopausal status; and, further, patients treated with the combination therapy attained better glycemic control than with either monotherapy.

It is to be understood, however, that for any particular subject being treated, e.g., a mammal, specific dosage regimens should be adjusted according to the individual need. It is further to be understood that the dosages set forth herein are examples only and that they do not, to any extent limit the scope of the practice of the present invention.

The core formulation of the present invention may be administered orally, for example, with inert diluent or with an edible carrier. For the purpose of oral therapeutic administration, the core formulation may have other excipients incorporated therein. The subject core formulation may also contain the following adjuvants: a binder such as microcrystalline cellulose, gum tragacanth or gelatin; an excipient such as starch or lactose, a disintegrating agent such as alginic acid, Primogel®, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring.

The subject core formulation of the invention may contain other various materials which modify the physical form of the dosage unit (the subject core formulation), for example, as coatings. Thus, the subject core formulation of the present invention may be coated with sugar, shellac or other enteric coating agents. Materials used in preparing these various compositions should be pharmaceutically pure and non-toxic in the amounts used.

In an alternative embodiment of the present invention. the resultant core formulation (having a first layer completely or partially covering the core), is treated whereby an outer shell is formed, at least a portion of which comprises the biodegradable modulating alginate material present is present in an amount having a predetermined rate of degradation or metabolism in the host being treated.

The biodegradable alginate material is a high molecular weight compound, which is physiologically acceptable and decomposes in the body of the human being or other animal and is absorbed.

The biodegradable alginate material, comprising the outer shell, having a predetermined rate of degradation or metabolism or break down, is selected from alginic acid, as well as single or mixed cationic salts of the free acid. Examples of these include sodium alginate, calcium alginate, sodium-calcium alginate, ammonium alginate, sodium-ammonium alginate, or calcium-ammonium alginate. Other materials, well known in the art, which do not react with metformin and/or troglitazone hydrochloride, such as, biodegradable polymers, including polyorthoesters, polyanhydrides, polyamides based on glutamic acid, polyalkyl cyanoacrylates, polyesters of lactic and glycolic acid, polyactide polymers, cellulosic polymers, polyvinyl acetate, polyvinyl alcohol, polyvinylchloride, natural and synthetic rubbers, polyacrylates, polystyrene, etc, may be used. Additionally, reference is made to U.S. Pat. Nos. 4,166,800, and 4,389,330, which disclose additional shell forming materials and are incorporated hereinto by reference in their entirety.

The shell encapsulating the particles of troglitazone hydrochloride of the first layer and/or the particles of metformin of the core is obtained by any conventional microencapsulation process whereby microspheres of metformin and/or troglitazone hydrochloride are formed, e.g. a solvent removal process, a phase separation technique, coacervation etc. In this regard reference is made to U.S. Pat. Nos. 4,166,800 and 4,389,330, Conte et al, *J. Controlled Release*, vol. 26, (1993), pages 39–47; and U.S. Pat. No. 4,839,177; all of which are incorporated hereinto by reference in their entirety.

In a variation of the above alternative embodiment, the resultant core formulation is treated whereby only the top surface area of the first layer comprising troglitazone hydrochloride has a shell coating thereon. In this regard, reference is made to U.S. Pat. No. 5,916,584, incorporated hereinto by reference in its entirety, which describes the process for forming such a shell. The resulting core formulation having the first layer encapsulated by the shell comprising the shell material, is one which provides a delay time prior to release of the active ingredients, i.e. troglitazone hydrochloride and metformin, to the patient being treated for diabetes mellitus.

In a second alternative embodiment of the present invention, the resultant core formulation (having a first layer completely or partially covering the core), is treated with a natural polysaccharide, in its free acid a or salt form, using a pharmaceutically accepted cation, for example, an alginate salt such as sodium, potassium, calcium, or ammonium; guar gum; gum arabic; gum karaya; gum Benjamin, plantago ovata gum; agar; carrageenan; cellulose; gelatin; pectin; or galacturonic acid to form a gel-like structure having a predetermined rate of modulated drug release effect, i.e. a timed drug release profile in the host being treated, which encloses the particles of the first layer and/or the core.

A suitable natural polysaccharide is one selected from the group of an alginate salt, e.g. $K^+$, $Na^+$, $Ca^{+2}$, $Li^{+1}$, $NH^{+3}$, $NH^{+3}$, (example Keltose™; International Specialty Products, 1361 Alps Road, Wayne, N.J. 07470). Alginates are naturally occurring polymers comprising polysaccharide chains. These polymers have the propensity to absorb water thus swelling to become gel like structures in solution. Upon ingestion of the resultant core formulation by a patient being treated, the gel dissolves in the body of such patient, e.g. in the stomach, thus releasing its drug payloads in a dissolution controlled manner.

As previously discussed, the natural polysaccharide polymer shell encapsulating the particles of troglitazone, e.g. its hydrochloride, of the first layer and/or the particles of metformin of the core is obtained by any conventional microencapsulation process whereby microspheres of metformin and/or troglitazone, e.g. its hydrochloride, are formed, e.g. a solvent removal process, a phase separation technique, coacervation etc. In this regard reference is made to U.S. Pat. Nos. 4,166,800 and 4,389,330, Conte et al, *J. Controlled Release*, vol. 26, (1993), pages 39–47; and U.S. Pat. No. 4,839,177; all of which are incorporated hereinto by reference in their entirety.

In a variation of the above alternative embodiment, the resultant core formulation is treated whereby only the top surface area of the first layer comprising troglitazone has a shell coating thereon. In this regard, reference is made to U.S. Pat. No. 5,916,584, incorporated hereinto by reference in its entirety, which describes the process for forming such a shell. The resulting core formulation having the first layer encapsulated by the shell comprising the polymer shell material, is one which provides a delay time prior to release of the active ingredients, i.e. troglitazone and metformin, to the patient being treated for diabetes mellitus.

The amount of the polymer employed will depend upon the medicament release profile desired, the particular polymer employed, the particular medicament or medicaments encapsulated or coated and the thickness of the coat of polymer contained on the particular medicament. Such amount can be readily determined by those of ordinary skill in the art with due consideration of the factors set forth above. Typically, for a release of about 2 to about 6 hours, the thickness ranges from about 0.0001 mm to about 1 mm with a concentration of the polymeric material ranging from about 10 ppm to about 100,000 ppm in one or both medicaments of the core to effect a desired release profile e.g. about 15 minutes to about 12 hours.

In a second alternative embodiment, the natural polysaccharide polymer, e.g. alginate, is first combined or mixed with at least one of the medicaments, e.g. the troglitazone hydrochloride first layer, whereafter the resultant core having the first layer thereon is prepared in any conventional manner, e.g. compression into a tablet.

The amount of the polymer combined or mixed with at least one of the medicaments, e.g. metformin, troglitazone, depends on the medicament release profile desired. This is readily determined by one of ordinary skill in the art. Typically, the effective concentration of the combined polymer for a particular drug, e.g. metformin, troglitazone, ranges from about 10 ppm to about 100,000 ppm in one or both medicaments of the core to effect a release profile of about 15 minutes to about 12 hours.

Accordingly, based upon the above discussion, the polysaccharide polymer, e.g. an alginate, is "associated" with the resultant core medicament. By "associated" or "association" is meant that the natural polysaccharide polymer, either fully or partially coats or encompasses the particles of at least one medicament, e.g. the first layer of troglitazone, or is combined or mixed with the particles of at least one medicament, e.g. metformin, prior to forming the resulting core medicament, in the formation of a modulate release core formulation.

It is again to be understood that for either metformin or troglitazone, any pharmaceutically acceptable form encompasses the free acids, free bases, salts and various hydrate forms, including semi-hydrate forms of these medicaments, as well as other pharmaceutical materials which are used in the formulation process as acceptable excipient materials generally known to those skilled in the art.

It is understood that any one of the biguanides, i.e. drugs having actions of stimulation of anaerobic glycolysis, is covered by this invention as these, like metformin, increase the sensitivity to insulin in peripheral tissues. These compounds also are involved in the inhibition of glucose absorption from the intestine, suppression of hepatic gluconeogenesis, and inhibition of fatty acid oxidation. Examples of other typical biguanides included in this application are phenformin, buformin etc.

We claim:

1. A core formulation comprising,
   (a) a first layer comprising troglitazone or a pharmaceutically acceptable salt thereof as an active ingredient,
   (b) a core, at least a portion of which is enclosed by said first layer, comprising a biguanide as an active ingredient; and
   (c) a polysaccharide polymer associated with at least one of said active ingredients.

2. The formulation as defined in claim 1 wherein said polymer is selected from the group consisting of an alginate salt, gum arabic, pectin, galacturonic acid, guar gum, gum karaya, gum Benjamin, plantago ovata gum, agar, carrageenan, cellulose, gelatin or any mixture of the foregoing polymers.

3. The formulation as defined in claim 1 wherein said first layer comprises troglitazone hydrochloride present in an amount ranging from about 1 mg to about 15 mg and said core comprises metformin present in an amount ranging from about 100 mg to about 500 mg.

4. The formulation as defined in claim 1, wherein said polymer is associated by forming a shell, having a predetermined rate of active ingredient release, covering at least a portion of said first layer to provide a predetermined delay in the time period of release of at least said troglitazone active ingredient.

5. The formulation as defined in claim 1, wherein said troglitazone and/or said biguanide are present as biodegradable microspheres with said polymer associated therewith by having a shell coating and where said shell coating has a predetermined rate of active ingredient release.

6. A method of administering troglitazone and metformin to a mammal, which comprises treating the mammal with the formulation defined in claim 3.

7. A method for producing a controlled release formulation, which comprises:
   (a) producing a hollow outer shell comprising a gel-like polysaccharide material having a predetermined rate of medicament release to provide a predetermined delay in the time period of release of the contents destined to be enclosed by said shell;
   (b) inserting a core, comprising metformin and having an outer layer comprising troglitazone partially enclosing said core, into said hollow outer shell; and (c) sealing said core within said hollow outer shell.

8. A method of producing a modulated release formulation of troglitazone hydrochloride medicament and metformin medicament, which comprises:

(a) forming a core of the metformin medicament; and (b) depositing a layer of the troglitazone hydrochloride medicament on at least a portion of a surface of said core; and (c) associating a polysaccharide polymer with at least one of the medicaments to form the modulated release formulation.

9. A method of treating diabetes mellitus in a patient in need thereof, which comprises administering to the patient the formulation of claim 1 wherein said active ingredients are each present in an effective amount.

10. A drug controlled-release pharmaceutical composition comprising an effective amount of troglitazone hydrochloride combined with an effective amount of metformin associated with an effective controlled-release amount of a polysaccharide polymer selected from the group consisting of an alginate, gum arabic, pectin, galacturonic acid, guar gum, gum karaya, gum Benjamin, plantago ovata gum, agar, carrageenan, cellulose, gelatin, or any mixture of the foregoing polymers.

11. A method of treating diabetes mellitus in a patient in need thereof, which comprises administering to the patient the composition of claim 10.

12. A drug controlled-release pharmaceutical composition comprising an effective amount of troglitazone hydrochloride combined with an effective amount of phenformin associated with an effective controlled-release amount of a polysaccharide polymer selected from the group consisting of an alginate, gum arabic, pectin, galacturonic acid, guar gum, gum karaya, gum Benjamin, plantago ovata gum, agar, carrageenan, cellulose, gelatin, or any mixture of the foregoing polymers.

13. A controlled-release pharmaceutical composition comprising an effective amount of troglitazone hydrochloride combined with an effective amount of buformin associated with an effective drug controlled-release amount of polysaccharide polymer selected from the group consisting of an alginate, gum arabic, pectin, galacturonic acid or any mixture of the foregoing polymers.

14. A method of treating diabetes mellitus in a patient in need thereof, which comprises, administering to the patient the composition of claim 12.

15. A method of treating diabetes mellitus in a patient in need thereof, which comprises, administering to the patient the composition of claim 13.

16. A method of treating diabetes mellitus in a patient in need thereof, which comprises, administering to the patient the composition of claim 1 wherein the biguanide is phenformin.

17. A method of treating diabetes mellitus in a patient in need thereof, which comprises, administering to the patient the composition of claim 1 wherein the biguanide is buformin.

18. A method of treating diabetes mellitus in a patient in need thereof, which comprises, administering to the patient the composition of claim 1 wherein the biguanide is metformin.

* * * * *